(12) United States Patent
Li et al.

(10) Patent No.: US 11,773,045 B2
(45) Date of Patent: Oct. 3, 2023

(54) ACID-CATALYZED PHOTOCATALYZED OXIDATION REACTION OF BENZYLIC C—H BONDS OF AROMATIC COMPOUND

(71) Applicant: Nanjing Tech University, Nanjing (CN)

(72) Inventors: Yufeng Li, Nanjing (CN); Hongjun Zhu, Nanjing (CN); Hongfei Ma, Nanjing (CN); Hongzhong Bu, Nanjing (CN); Jieqing Wu, Nanjing (CN); Jiefan Gu, Nanjing (CN); Jiwei Chen, Nanjing (CN); Haoyue Zhang, Nanjing (CN); Chen Wang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 18/024,730

(22) PCT Filed: Jan. 19, 2022

(86) PCT No.: PCT/CN2022/072634
§ 371 (c)(1),
(2) Date: Mar. 3, 2023

(87) PCT Pub. No.: WO2023/070961
PCT Pub. Date: May 4, 2023

(65) Prior Publication Data
US 2023/0242470 A1    Aug. 3, 2023

(30) Foreign Application Priority Data

Oct. 29, 2021   (CN) .......................... 202111273648.2

(51) Int. Cl.
*C07C 51/16* (2006.01)
*C07C 45/32* (2006.01)
(Continued)

(52) U.S. Cl.
CPC .............. *C07C 51/16* (2013.01); *C07C 45/32* (2013.01); *C07C 201/12* (2013.01); *C07C 253/30* (2013.01)

(58) Field of Classification Search
None
See application file for complete search history.

(56) References Cited

U.S. PATENT DOCUMENTS 2,833,816 A    5/1958  Saffer
2004/0015009 A1*    1/2004  Earle ...................... C07C 51/27
562/409

FOREIGN PATENT DOCUMENTS

CN    1469856 A    1/2004
CN    1810754 A    8/2006
(Continued)

OTHER PUBLICATIONS

Liu, Jing et al., Aerobic oxidation of C—H bonds to carboxylic acids enabled by decatungstate photocatalysis, Green Synthesis and Catalysis, 2021, pp. 389-392.
(Continued)

*Primary Examiner* — Sudhakar Katakam
*Assistant Examiner* — Jennifer C Sawyer
(74) *Attorney, Agent, or Firm* — KIRTON McCONKIE; Evan R. Witt (57) ABSTRACT

Provided is a photo-oxidation reaction of benzylic C—H bonds of an aromatic compound under the catalysis of an acid catalyst. The method aims to synthesize aromatic acids and acetophenones. The acid catalyst is one of Bronsted acids, including one or a mixture of two or more selected from the group consisting of hydrochloric acid, phosphoric acid, sulfuric acid, p-toluenesulfonic acid, methanesulfonic acid, trifluoromethanesulfonic acid, trifluoroacetic acid, and potassium hydrogen sulfate, as well as N-propylsulfonate pyridinium hydrogensulfate, N-butylsulfonate pyridinium
(Continued)

$R^1 = R^2 = R^3 = H$;
$X = Me$, $OMe$, halogen(F, Cl, Br, I), $o$ ($m$, or $p$)-$CF_3$.

$R^1 = Me$, $R^2 = R^3 = H$; or $R^1 = R^2 = R^3 = Me$;
$X =$ halogen(F, Cl, Br, I), $o$ ($m$, or $p$)-$CF_3$, $m$(or $p$)-$NO_2$ hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate. The oxidation reaction is conducted under mild conditions (normal temperature and pressure) using air or oxygen as the oxidant in the presence of recyclable catalyst and solvent.

20 Claims, 1 Drawing Sheet

(51) Int. Cl.
    *C07C 201/12*     (2006.01)
    *C07C 253/30*     (2006.01)

(56) References Cited

FOREIGN PATENT DOCUMENTS

| | | |
|---|---|---|
| CN | 109836307 A | 6/2019 |
| CN | 110563571 A | 12/2019 |
| CN | 111960936 A | 11/2020 |

OTHER PUBLICATIONS

Huang, Zhiliang et al., Chemical Recycling of Polystyrene to Valuable chemicals via Selective Acid-Catalyzed Aerobic Oxidation under Visible Light, Journal of the American Chemical Society, 2022, pp. 6532-6542.
Niu, Kaikai et al., HCl-Catalyzed Aerobic Oxidation of Alkylarenes to Carbonyls, ChemSusChem, 2022, pp. 1-5.
Zhu, Xianjin et al., Light and oxygen-enabled sodium trifluoromethanesulfinate-mediated selective oxidation of C—H bonds, Green Chemistry, 2020, pp. 4357-4363.
Bikash, Bidyut et al., Oxygenation of Methylarenes to Benzaldehyde Derivatives by a Polyoxometalate Mediated Electron Transfer-Oxygen Transfer Reaction in Aqueous Sulfuric Acid, Journal of the American Chemical Society, 2015, pp. 5916-5922.
Mardani, Atefeh et al., Photo-tunable oxidation of toluene and its derivatives catalyzed by TBATB, Journal of Photochemistry & Photobiology, 2021, pp. 1-8.
Wang, Chang-Cheng et al., Photo-induced deep aerobic oxidation of alkyl aromatics, Science China Chemistry, 2021, pp. 1-6.
Tamai, Kazuki et al., Visible-Light Selective Photooxidation of Aromatic Hydrocarbons via Ligand-to-Metal Charge Transfer Transition on Nb2O5, The Journal of Physical Chemistry, 2017, pp. 22854-22861.
Tripathy, Jyotsna et al., Tuning the Selectivity of Photocatalytic Synthetic Reactions Using Modified TiO2 Nanotubes, 2014, pp. 12605-12608.
Ishii, Yasutaka et al., Alkane Oxidation with Molecular Oxygen Using a New Efficient Catalytic System: N-Hydroxyphthalimide (NHPI) combined with Co(acac)n (n=2 or 3), J. Org. Chem., vol. 61. No. 14, 1996, pp. 4520-4526.
Sarma, Daisy et al., Carboxyl-functionalized Carbon Dots as Competent Visible Light Photocatalysts for Aerobic Oxygenation of Alkyl Benzenes: Role of Surface Functionality, ACS Sustainable chem. Eng., 2018, pp. 16573-16585.
Song, Lu-Na et al., Synthesis of TiO2/Bi2MoO6 Composite for Partial Oxidation of Aromatic Alkanes under Visible-Light Illumination, ACS Sustainable Chem. Eng. 2018, pp. 17044-17050.
Liu, Ying et al., A green and efficient photocatalytic route for the highly-selective oxidation of saturated alpha-carbon C—H bonds in aromatic alkanes over flower-like Bi2WO6, Chem. Commun., 2016, pp. 1274-1277.
Ide, Yusuke et al., Zeolitic intralayer microchannels of magadiite, a natural layered silicate, to boost green organic synthesis, Chem. Sci., 2018, pp. 8637-8643.
Itoh, Akichika et al., Aerobic Photooxidation of Methyl Group at Aromatic Nucleus with LiBr, Synlett, 2005, pp. 2107-2109.
Sugai, Taichi et al., Aerobic oxidation under visible light irradiation of a fluorescent lamp with a combination of carbon tetrabromide and triphenyl phosphine, Tetrahedron Letters, 2007, pp. 9096-9099.
Muhldorf, Bernd et al., C—H Photooxygenation of Alkyl Benzenes Catalyzed by Riboflavin Tetraacetate and a Non-Heme Iron Catalyst, Angew. chem. Int. Ed, 2016, pp. 427-430.
Pan, Decheng et al., Visible-Light-Induced Aerobic Oxidation of Benzylic C(sp3)-H of Alkylarenes Promoted by DDQ, tert-Butyl Nitrite, and Acetic Acid, Synlett, 2019, pp. 218-224.
Muhldorf, Bernd et al., Photocatalytic benzylic C—H bond oxidation with a flavin scandium complex, Chem. Commun., 2015, pp. 8425-8428.
Xia, Lei et al., Benzaldehyde Schiff bases regulation to the metabolism, hemolysis, and virulence genes expression in vitro and their structure-microbicidal activity relationship, European Journal of Medicinal Chemistry, 2015, pp. 83-93.
Li, Qing et al., Rapid generation of novel benzoic acid-based xanthine derivatives as highly potent, selective and long acting DPP-4 inhibitors: Scaffold-hopping and prodrug study, European Journal of Medicinal Chemistry, 2019, pp. 509-523.
Lechner, Robert et al., Visible light flavin photo-oxidation of methylbenzenes, styrenes and phenylacetic acids, Photochem. Photobiol. Sc., 2019, pp. 1367-1377.
Xu, Weicheng et al., Designing a dumbbell-brush-type Co3O4 for efficient catalytic toluene oxidation, Catalysis Communications, 2020, 1-5.
Weng, Xiaoyu et al., Highly dispersed Pd/modified-Al2O3 catalyst on complete oxidation of toluene: Role of basic sites and mechanism insight, Applied Surface Science, 2019, pp. 1-11.
Sun, Hong et al., Catalytic oxidation of toluene over manganese oxide octahedral molecular sieves (OMS-2) synthesized by different methods, Chemical Engineering Journal, 2011, pp. 191-196.
Hirai, Naruhisa et al., Oxidation of Substituted Toluenes with Molecular Oxygen in the Presence of N,N,N-Trihydroxyisocyanuric Acid as a Key Catalyst, J. Org. Chem., 2003, pp. 6587-6590.
Li, Sanliang et al., Visible light-induced selective aerobic oxidative transposition of vinyl halides using a tetrahalogenoferrate(III) complex catalyst, Org. chem. Front., 2018, pp. 380-385.
Partenheimer, W., Methodology and scope of metal/bromide autoxidation of hydrocarbons, Catalysis Today, 1995, pp. 69-158.
Takaki, Ken et al., Oxidation of Alkanes with Dioxygen Induced by Visible Light and Cu(II) and Fe (III) Chlorides, Bull. Chem. Soc. Jpn., 2003, pp. 393-398.
Rosenthal, Joel et al., Photocatalytic Oxidation of Hydrocarbons by a Bis-iron(III)-u-oxo Pacman Porphyrin Using O2 and Visible Light, J. Am. Chem. Soc., 2006, pp. 6546-6547.

* cited by examiner

ACID-CATALYZED PHOTOCATALYZED OXIDATION REACTION OF BENZYLIC C—H BONDS OF AROMATIC COMPOUND

CROSS REFERENCE TO RELATED APPLICATION

The present disclosure claims the priority to Chinese Patent Application CN202111273648.2, titled "ACID-CATALYZED PHOTOCATALYZED OXIDATION REACTION OF BENZYLIC C—H BONDS OF AROMATIC COMPOUND", filed with China National Intellectual Property Administration (CNIPA) on Oct. 29, 2021, which is incorporated herein by reference in its entirety.

TECHNICAL FIELD

The present disclosure belongs to the field of chemical synthesis, and in particular relates to an acid-catalyzed photo-oxidation reaction. In the present disclosure, methyl, ethyl, and cumenes are oxidized under mild conditions to obtain useful aromatic acids or acetophenones.

BACKGROUND

Aromatic acids and acetophenones are widely-used intermediates for synthesis of various drugs, pesticides and other chemicals. Aromatic acids are traditionally synthesized by hydrolysis of benzyl trichloride intermediates and oxidation of methylarenes with high-valent metal oxidant. Acetophenones are generally prepared by Friedel-Crafts acylation. These traditional methods usually require a large amount of chemicals or excessive amount of other reagents (raw materials). These methods, lacking of atom- and step economy and generating a large amount of wastes that are difficult to handle, are environmentally hazardous and economically high-cost. The clean oxidation of benzylic C—H bonds of aromatic compounds to obtain useful intermediates such as aldehydes, ketones, or acids is more economical and environmentally friendly. In 1958, Amoco applied the metal-catalyzed aerobic liquid-phase oxidation technology (1958, U.S. Pat. No. 2,833,816) to the industrial production of terephthalic acid. However, this craft adopt acetic acid and bromine that are extremely corrosive to the equipment, and requires a complicated process. Meanwhile, in the case of other reported crafts, the catalysts adopted either are unrecyclable due to catalyst-destruction or have lower catalytic efficiency, thus showing unreliable industrial application prospects.

SUMMARY

The present disclosure provides an acid-catalyzed photocatalyzed oxidation reaction of benzylic C—H bonds of an aromatic compound, where the liquid-phase oxidation reaction is conducted with oxygen or air as the oxidants using Bronsted acid as the photocatalyst at normal pressure under light irradiation with a wavelength range of 300 nm to 450 nm.

In some examples, the Bronsted acid is one or a mixture of two or more selected from the group consisting of an inorganic acid, an organic acid, and an acidic ionic liquid.

In some examples, the Bronsted acid is one or a mixture of two or more selected from the group consisting of hydrochloric acid, phosphoric acid, sulfuric acid, p-toluenesulfonic acid, methanesulfonic acid, trifluoromethanesulfonic acid, trifluoroacetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

In some examples, the Bronsted acid is one or a mixture of two or more selected from the group consisting of hydrochloric acid, sulfuric acid, tetrafluoroboric acid, p-toluenesulfonic acid, methanesulfonic acid, trifluoromethanesulfonic acid, trifluoroacetic acid, acetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

In some examples, aromatic compound is one selected from the group consisting of methyarenes, ethylarenes, or cumenes-that contains at least one benzylic C—H bond.

In some examples, the oxidized aromatic compound is selected from the group consisting of the methylarenes, the ethylarenes, and the cumenes; the methylarenes are selected from the group consisting of toluene, o-xylene, m-xylene, p-xylene, mesitylene, toluene substituted with 1 to 3 halogen atoms, toluene substituted with alkoxy of 1 to 2 C atoms, and trifluoromethyl-substituted toluene; the ethylarenes are selected from the group consisting of ethylbenzene, p-diethylbenzene, ethylbenzene substituted with 1 to 3 halogen atoms, ethylbenzene substituted with alkoxy of 1 to 2 C atoms, trifluoromethyl-substituted ethylbenzene, and nitro-substituted ethylbenzene; and the cumenes are selected from the group consisting of cumene, halogen-substituted cumene, trifluoromethyl-substituted cumene, and nitro-substituted cumene.

In some examples, the oxidized aromatic compound is selected from the group consisting of the methylarenes, the ethylarenes, and the cumenes; the methylarenes are any one selected from the group consisting of toluene, o-xylene, m-xylene, p-xylene, mesitylene, toluene substituted with 1 to 3 halogen atoms, toluene substituted with alkoxy of 1 to 2 C atoms, trifluoromethyl-substituted toluene, o-tolunitrile, m-tolunitrile, p-tolunitrile, o-toluic acid, m-toluic acid, p-toluic acid, 2-methyl diphenyl, 3-methyl diphenyl, and 4-methyl diphenyl; the ethylarenes are any one selected from the group consisting of ethylbenzene, p-diethylbenzene, ethylbenzene substituted with 1 to 3 halogen atoms, ethylbenzene substituted with alkoxy of 1 to 2 C atoms, trifluoromethyl-substituted ethylbenzene, and nitro-substituted ethylbenzene; and the cumenes are any one selected from the group consisting of cumene, halogen-substituted cumene, trifluoromethyl-substituted cumene, and nitro-substituted cumene.

In some examples, the oxidation reaction is conducted in a solvent; the solvent is selected from the group consisting of water, dichloromethane, dichloroethane, benzene, chlorobenzene, acetonitrile, acetone, 2-butanone, and the ionic liquid; and the ionic liquid is one selected from the group consisting of N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate, or is a mixture of two of the above-described solvents.

In some examples, the oxidation reaction is conducted in a solvent, and the solvent is selected from the group consisting of water, the organic solvent, and the ionic liquid, or is a mixture of two of the solvent. In some examples, the organic solvent is at least one selected from the group consisting of dichloromethane, dichloroethane, chloroform, benzene, chlorobenzene, acetonitrile, acetone, and 2-butanone. In some examples, the ionic liquid is at least one selected from the group consisting of the N-propylsulfonate pyridinium hydrogensulfate, the N-butylsulfonate pyridinium hydrogensulfate, the N-propylsulfonate pyridinium trifluoromethanesulfonate, the N-butylsulfonate pyridinium trifluoromethanesulfonate, the N-propylsulfonate pyridinium tetrafluoroborate, and the N-butylsulfonate pyridinium tetrafluoroborate.

In some examples, the oxidation reaction is conducted in the solvent; the Bronsted acid includes the inorganic acid; the solvent is selected from the group consisting of water, the organic solvent, or a mixture of water and the organic solvent. In some examples, the organic solvent is one or a mixture of two or more selected from the group consisting of the dichloromethane, the dichloroethane, the chloroform, the benzene, the chlorobenzene, the acetonitrile, the acetone, and the 2-butanone.

In some examples, the oxidation reaction is conducted in the solvent; the Bronsted acid includes the organic acid; the solvent is selected from the group consisting of the organic solvent and the mixture of the organic solvent and water. In some examples, the organic solvent is one selected from the group consisting of the dichloromethane, the dichloroethane, the benzene, the chlorobenzene, the chloroform, the acetonitrile, the acetone, and the 2-butanone.In some examples, the oxidation reaction is conducted in the solvent; the Bronsted acid includes a strongly-acidic ionic liquid; and the solvent is a mixture of one selected from the group consisting of the dichloromethane, the dichloroethane, the benzene, the chlorobenzene, and the chloroform with water.

In some examples, the Bronsted acid is used with an amount of 0.1% mol to 20% mol of the aromatic compound.

In some examples, the Bronsted acid is used with an amount of 0.5% mol to 5% mol of the aromatic compound.

In some examples, a product obtained by photo-oxidation of the methylarenes under acid catalysis is a corresponding substituted or unsubstituted aryl fomic acid; a product obtained by photo-oxidation of the ethylarenes under acid catalysis is a corresponding substituted or unsubstituted acetophenone; and a product obtained by photo-oxidation of the cumenes under acid catalysis is a corresponding acetophenone.

In some examples, the oxidation reaction is conducted at 10° C. to 100° C.

In some examples, the oxidation reaction is conducted at 20° C. to 60° C.

DETAILED DESCRIPTION OF THE EMBODIMENTS

Figure 1:
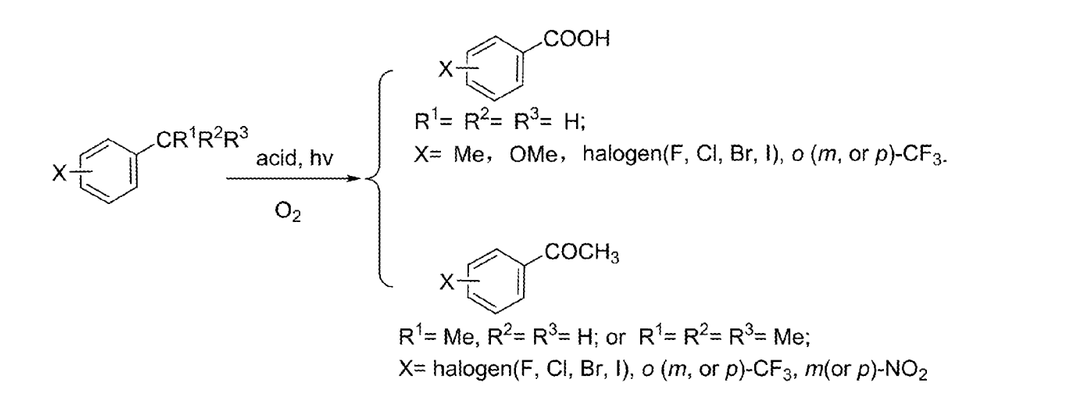
FIG. 1 shows a reaction chemical formula of acid-catalyzed air oxidation of a benzylic C—H bond of an aromatic compound under light irradiation according to some examples of the present disclosure.

The technical solutions of the present disclosure will be further clearly described with the following examples. Obviously, the limited examples do not limit the claims of the present disclosure.

Aromatic acids or acetophenones are synthesized with high selectivity and high yield by photo-oxidation on a benzylic C—H bond of an aromatic compound using Bronsted acids as a catalyst under light irradiation. The reaction is conducted at 300 nm to 450 nm of ultraviolet or blue light irradiation. The catalyst is an acidic substance.

In some examples, the acidic catalysts each are Bronsted acids, including highly-acidic inorganic acids, organic acids, acidic ionic liquids, and hydrogen sulfate. In some examples, the Bronsted acid is one or a mixture of two or more selected from the group consisting of an inorganic acid, an organic acid, and an acidic ionic liquid. In some examples, the acidic ionic liquid may be selected from pyridinium salt-typed acidic ionic liquids.

In some examples, Bronsted acid catalyst includes, but is not limited to one or a mixture of two or more selected from the group consisting of hydrochloric acid, phosphoric acid, sulfuric acid, p-toluenesulfonic acid, methanesulfonic acid, trifluoromethanesulfonic acid, trifluoroacetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate. In some examples, the Bronsted acid is one or a mixture of two or more selected from the group consisting of hydrochloric acid, sulfuric acid, tetrafluoroboric acid, p-toluenesulfonic acid, methanesulfonic acid, trifluoromethanesulfonic acid, trifluoroacetic acid, acetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate. In some examples, the inorganic acidic species may be, for example, sulfuric acid. In some examples, the organic acidic species may be, for example, N-propylsulfonate pyridinium trifluoromethanesulfonate.

In some examples, the catalyst is used with an amount of 0.1% mol to 20% mol of the aromatic compound. In some examples, the catalyst is used with an amount of 0.5% mol to 5% mol of the aromatic compound. The raw material is an alkyl aromatic compound with a substituent-containing or substituent-free benzene ring.

In the acid-catalyzed photo-oxidation method, the raw material (an oxidized aromatic compound) is selected from the group consisting of methylarenes, ethylarenes, and cumenes that contain one benzylic C—H bond. In some examples, the methylarenes are selected from the group consisting of toluene, o-xylene, m-xylene, p-xylene, mesitylene, toluene substituted with 1 to 3 halogen atoms, toluene substituted with alkoxy of 1 to 2 C atoms, trifluoromethyl-substituted toluene, and nitro-substituted toluene. In some examples, the methylarenes are any one selected from the group consisting of toluene, o-xylene, m-xylene, p-xylene, mesitylene, toluene substituted with 1 to 3 halogen atoms, toluene substituted with alkoxy of 1 to 2 C atoms, trifluoromethyl-substituted toluene, o-tolunitrile, m-tolunitrile, p-tolunitrile, o-toluic acid, m-toluic acid, p-toluic acid, 2-methyl diphenyl, 3-methyl diphenyl, and 4-methyl diphenyl. In some examples, the ethylarenes are selected from the group consisting of ethylbenzene, p-diethylbenzene, ethylbenzene substituted with 1 to 3 halogen atoms, ethylbenzene substituted with alkoxy of 1 to 2 C atoms, trifluoromethyl-substituted ethylbenzene, and nitro-substituted ethylbenzene. In some examples, the cumenes are selected from the group consisting of cumene, halogen-substituted cumene, trifluoromethyl-substituted cumene, and nitro-substituted cumene.

In some examples, an oxidant of the oxidation reaction is air or oxygen. The gas can be communicated with a reactor using a tee joint, and can also be introduced into a bottom of the reaction solution by bubbling.

In some examples, the oxidation reaction is conducted by a gas-liquid phase reaction, with a solvent being one or a mixture of two selected from the group consisting of water, dichloromethane, dichloroethane, benzene, chlorobenzene, acetonitrile, acetone, and 2-butanone, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate. In some examples, the oxidation reaction is conducted by a gas-liquid phase reaction, with a solvent being one or a mixture of two selected from the group consisting of water, dichloromethane, dichloroethane, chloroform, benzene, chlorobenzene, acetonitrile, acetone, and 2-butanone, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

In some examples, if the oxidation reaction adopts an inorganic acid, such as hydrochloric acid, phosphoric acid, sulfuric acid, tetrafluoroboric acid, and potassium hydrogen sulfate as a catalyst, correspondingly, water can be used as a solvent, or a stable organic solvent incompatible with water, such as dichloromethane, dichloroethane, chloroform, benzene, and chlorobenzene can be used as the solvent, or water-miscible acetonitrile, acetone, and 2-butanone can be used as the solvent.

In some examples, if the oxidation reaction adopts the organic acidic substances, such as methanesulfonic acid, p-toluenesulfonic acid, trifluoromethanesulfonic acid, trifluoroacetic acid, and acetic acid as a catalyst, correspondingly, any one of dichloromethane, dichloroethane, chloroform, benzene, chlorobenzene, acetonitrile, acetone, and 2-butanone in the organic solvents, or a mixed solvent thereof with water can be used.

In some examples, if the oxidation reaction adopts several types of ionic liquids (strongly-acidic ionic liquids) among the organic acidic substances as a catalyst, such as hydrogen sulfate ionic liquid, tetrafluoroborate ionic liquid, and trifluoromethanesulfonate ionic liquid, a mixed solvent prepared by any one of the organic solvents including dichloromethane, dichloroethane, benzene, and chlorobenzene with water can be used. In some examples, the oxidation reaction adopts the trifluoromethanesulfonate ionic liquid in the acidic ionic liquid as a catalyst, and correspondingly, acetonitrile, acetone, and 2-butanone with better solubility can be used alone as a solvent. In some examples, if the oxidation reaction adopts several types of ionic liquids among the organic acidic substances as a catalyst, correspondingly, they can also be used as a reaction solvent.

In some examples, the acid-catalyzed photo-oxidation reaction is the direct oxidation of the benzylic C—H bond of the aromatic compound to obtain the aromatic acids or acetophenones. If the aromatic compound is methylarenes, a resulting product is the corresponding aromatic acid; if the aromatic compound is ethylarenes, a resulting product is the corresponding acetophenone; if the aromatic compound is cumenes, a resulting product is the corresponding acetophenone.

In some examples, the substrate is o- (or m- and p-) xylene and a resulting product is the corresponding o- (m- or p-) toluic acid. In some examples, the substrate is mesitylene and a resulting product is 3,5-dimethylbenzoic acid. In some examples, when the substrate is methoxy (or ethoxy)-substituted toluene, a resulting main product is the corresponding methoxy (or ethoxy)-benzoic acid. In some examples, the substrate is halogenated toluene substituted with a benzene ring of 1 to 3 halogen (fluorine, chlorine, bromine, or iodine), o-trifluoromethyltoluene, m-trifluoromethyltoluene, or p-trifluoromethane toluene, and a resulting product is the corresponding halogenated benzoic acid, o-trifluoromethylbenzoic acid, m-trifluoromethylbenzoic acid, or p-trifluoromethylbenzoic acid. The substrate is o-tolunitrile, m-tolunitrile, or p-tolunitrile, and a resulting product is the corresponding o-cyanobenzoic acid, m-cyanobenzoic acid, or p-cyanobenzoic acid. The substrate is o-toluic acid, m-toluic acid, or p-toluic acid, and a resulting product is the corresponding o-phthalic acid, m-phthalic acid, or p-phthalic acid. The substrate is 2-methyl diphenyl, 3-methyl diphenyl, or 4-methyl diphenyl, and a resulting product is the corresponding 2-biphenylcarboxylic acid, 3-biphenylcarboxylic acid, or 4-biphenylcarboxylic acid. In some examples, the substrate is p-diethylbenzene and resulting products are p-ethylacetophenone and p-diacetylbenzene. In some examples, the substrate is ethylbenzene substituted with 1 to 3 halogen atoms, ethylbenzene substituted with 1 to 2 alkoxy, trifluoromethyl-substituted ethylbenzene, and nitro-substituted ethylbenzene, to obtain the corresponding acetophenones. In some examples, the substrate is cumene, cumene substituted with 1 to 3 halogen atoms, trifluoromethyl-substituted cumene, nitro-substituted cumene, and a product obtained by oxidation is the corresponding acetophenones.

In some examples, the acid-catalyzed photo-oxidation reaction is conducted at 10° C. to 100° C. In some examples, the acid-catalyzed photo-oxidation reaction is conducted at 20° C. to 60° C. A wider temperature range can be used when using a non-ionic liquid solvent; when using the ionic liquid as a solvent as well as a catalyst, the reaction must be conducted at not less than 45° C.

The oxidation of alkylbenzenes can be divided into gas-phase oxidation and liquid-phase oxidation according to process conditions. The research on gas-phase oxidation mostly focuses on the oxidation of toluene to aldehyde, which commonly sacrifice conversion yields to obtain an acceptable selectivity, and thus show an unclear industrial application value (*Chemical Engineering Journal*, 2011, 178: 191-196.; *Angewandte Chemie, International Edition*, 2014, 53 (46): 12605-12608.; *Catalysis Communications*, 2020, 140: 106005.; *Applied Surface Science*, 2019, 497: 143747.). The liquid-phase oxidation of benzylic C—H bonds of the alkylbenzenes can obtain aromatic aldehydes, ketones, and acids. Due to the difficulty of equipment fabrication, photocatalytic reactions are generally used for liquid-phase oxidation. The catalysts used include: bromine-containing substances (*Tetrahedron Letters*, 2007, 48: 9096-9099.; *Synlett*, 2005, 13: 2107-2109.), iron, cobalt metal salts (*Bull. Chem. Soc. Jpn.*, 2003, 76 (2): 393-398.; *J. Am. Chem. Soc.*, 2006, 128 (20): 6546-6547.; *Org. Chem. Front.*, 2018, 5 (3): 380-385.; *J. Org. Chem.*, 2003, 68 (17): 6587-6590.; *J. Org. Chem.*, 1996, 61 (14): 4520-4526.; *Catal. Today*, 1995, 23 (2): 69-158. CN202010768698.7), organic photosensitive substances (*Synlett*, 2019, 30(02):

218-224.; *Eur. J. Med. Chem.*, 2019, 180, 509-523.; *Eur. J. Med. Chem.*, 2015, 97: 83-93.; *Chem. Commun.*, 2015, 51: 8425-8428.; *Angew. Chem. Int. Ed.*, 2016, 55: 427-430.; *Photochem. Photobiol. Sci.*, 2010, 9 (10): 1367-1377.), and semiconductor materials (*Chem. Commun.*, 2016, 52 (6): 1274-1277.; *J. Phys. Chem. C*, 2017, 121 (41): 22854-22861.; *ACS Sustain. Chem. Eng.*, 2018, 6 (12): 17044-17050.; *Chem. Sci.*, 2018, 9 (46): 8637-8643.; *ACS Sustain. Chem. Eng.*, 2018, 6: 16573-16585.).

A purpose of the present disclosure is to overcome the deficiencies in the existing technology for benzylic oxidation of aromatic compounds, such as the complex operational conditions at high temperature, high pressure and equipment corrosion in the AMOCO method or similar processes, and the high cost, poor recyclability, or low catalytic efficiency of catalysts used in those photocatalytic oxidation methods.

In the present disclosure, the Bronsted acid (Bronsted acid) is used as a catalyst under ultraviolet or visible light irradiation, alkylbenzene-based aromatic hydrocarbons are oxidized into the aromatic acids and acetophenones with high selectivity using air or oxygen. The reaction in this method can obtain good conversion rate and conversion yield under mild conditions. According to an extensive literature survey, the readily attainable Bronsted acid has not yet been reported in the literature as a photo catalyst alone without exogenous photosensitizer.

(1) In the present disclosure, since there are no academic papers and patent reports on the photo-oxidation reaction using Bronsted acid exclusively as the photo catalyst, the acid-catalyzed photo-oxidation of methylarenes is a technically novel reaction method.

(2) In the present disclosure, the acid-catalyzed photo-oxidation reaction of methylarenes has significant technical advantages, and its oxidation process has no metal participation, no chemical oxidants, mild reaction conditions, fast conversion, and high selectivity. In addition, the catalyst is not consumed and can be easily recovered. The reaction has high atom economy, clean process, and low-cost oxidant, showing a desirable prospect of industrial application.

(3) In the present disclosure, the acid-catalyzed photo-oxidation reaction of methylarenes has desirable industrialization prospects, and has significant advantages in safety, environmental protection, economic and social benefits.

The acid-catalyzed photo-oxidation reaction of methylarenes is conducted under a normal pressure. Although a high oxygen pressure helps to accelerate the reaction theoretically, the reaction safety and the difficulty for the design of photo autoclave reactor should be considered.

EXAMPLES

The present disclosure is further described below with reference to examples. It should be noted that the following examples are only exemplary examples of the present disclosure, and do not limit the claims and descriptions of the present disclosure.

In the following examples: liquid chromatography external standard method included: with reference to GB/T 5009.29-2003, adopting a high-performance liquid chromatography: Ultimate 3000 (2017LH132); detector: diode array; detection wavelength: 230 nm; chromatographic column: Accucore C18 (2.1 mm×150 mm); flow rate: 0.2 mL/min; injection volume: 2 μL; column temperature: 30° C.; mobile phase: methanol/phosphate buffer (1/1, V:V).

A detection method of gas chromatography-mass spectrometry was as follows: Thermo Fisher Scientific, TRACE1300ISQLT GC/MS, ionization mode, MS Transfer line temp 300° C., temperature program: 50° C./10 min to 300° C./10 min.

Liquid chromatography-mass spectrometer: Thermo Fisher Scientific, LCQ/Advantage LC/MS, electrospray (ESI) ionization source, flow rate: 0.2 mL/min; injection volume: 1 μL; column temperature: 30° C.; flow phase: methanol/water (5/95, V:V).

Example 1

Acid-Catalyzed Photo-Oxidation Reaction of Toluene 2 mmol of hydrochloric acid (concentrated hydrochloric acid), 5 mL of water, 10 mmol of toluene, and 5 mL of acetone were sequentially added to a 25 mL colorless and transparent ground quartz tube with a built-in magnetic stirring bar. A condenser was attached to the test tube for air communication. The reaction mixture was stirred and irradiated by a 50 W UV light source with a wavelength of 350 nm to 370 nm for 16 h. The reaction was monitored by GC-MS with deduction of the solvent absorption, consisting of 10.5% of benzyl chloride, 2.3% of benzaldehyde, and 74.6% of benzoic acid. The reaction was terminated, and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 20% hydrochloric acid. The mixture was filtered, and the obtained solid was dried to obtain 0.82 g of a white benzoic acid solid with an isolated yield of 67.0%, having a purity of 97.7% by the liquid chromatography external standard analysis.

Example 2

Acid-Catalyzed Photo-Oxidation Reaction of p-xylene—Synthesis of p-toluic Acid 2 mmol of phosphoric acid (with a mass fraction of 85%), 3 mL of water, 10 mmol of p-xylene, and 7 mL of dichloroethane were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W UV light source with a wavelength of 350 nm to 370 nm for 48 h. The reaction was monitored by GC-MS with deduction of the solvent absorption, consisting of 30.8% of p-xylene, 18.5% of p-tolualdehyde, and 45.4% of p-toluic acid. The organic layers were combined, and then washed thoroughly with a saturated sodium carbonate water solution (5 mL×2). The resulted water layers were combined and acidified to pH=2 to 3 with 20% hydrochloric acid. The mixture was filtered, and the obtained solid was dried to obtain 0.53 g of a white p-toluic acid solid with an isolated yield of 67.0%, having a purity of 39.0% by the liquid chromatography external standard analysis

Example 3

Acid-Catalyzed Photo-Oxidation of Mesitylene 2 mmol of sulfuric acid, 3 mL of water, 10 mmol of mesitylene, and 7 mL of acetonitrile were sequentially added to a 25 mL colorless and transparent ground quartz tube with a built-in magnetic stirring bar. A condenser was attached to the test tube for air communication. The reaction mixture was stirred and irradiated by a 50 W light source with a wavelength of 395 nm to 405 nm for 24 h. The reaction was monitored by LC-MS with deduction of the solvent absorption, consisting of 2.6% of 3,5-dimethylbenzyl chloride, 1.4% of 3,5-dimethylbenzaldehyde, 2.4% of 3,3',5,5'-tetramethylbibenzyl, 75.6% of 3,5-methylbenzoic acid, and 1.8% of 3-methyl m-phthalic acid. The reaction was terminated, and the acetonitrile was removed by rotary evaporation under reduced pressure; the reaction mixture was extracted with dichloromethane (10 mL×3). The organic layers were combined, and then washed thoroughly with a saturated sodium carbonate water solution (5 mL×2). The resulted water layers were combined and acidified to pH=2 to 3 with 10% sulfuric acid. The mixture was filtered, and the obtained filter cake was dried to obtain 0.965 g of a white 3,5-dimethylbenzoic acid solid with an isolated yield of 65.2%, having a purity of 97.6% by the liquid chromatography external standard analysis.

Example 4

Acid-Catalyzed Photo-Oxidation of p-chlorotoluene 0.5 mmol of methanesulfonic acid, 10 mmol of p-chlorotoluene, and 5 mL of dichloromethane were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W light source with a wavelength of 395 nm to 405 nm for 17 h. The reaction was monitored by LC-MS with deduction of the solvent absorption, consisting of 0.6% of p-chlorobenzyl chloride, 0.9% of p-chlorobenzaldehyde, 3.2% of 4,4'-dichlorobibenzyl, and 64.3% of p-chlorobenzoic acid. The reaction was terminated, and the acetonitrile was removed by rotary evaporation under reduced pressure; the reaction mixture was extracted with dichloromethane (10 mL×3). The organic layers were combined, and then washed thoroughly with a saturated sodium carbonate water solution (5 mL×2). The resulted water layers were combined and acidified to pH=2 to 3 with 10% sulfuric acid. The mixture was filtered, and an obtained filter cake was dried to obtain 0.92 g of a white p-chlorobenzoic acid solid with an isolated yield of 58.5%, having a purity of 98.4% by the liquid chromatography external standard analysis.

Example 6

Acid-Catalyzed Photo-Oxidation of p-fluorotoluene 1 mmol of N-(4-sulfobutyl)pyridinium hydrogensulfate, 1 mL of water, and 10 mmol of p-fluorotoluene were sequentially added to a 25 mL colorless and transparent ground quartz tube with a built-in magnetic stirring bar. The test tube was connected to a tee and then connected with an oxygen-filled balloon. A heating knob of the bottom plate was adjusted to raise a reaction solution to 40° C. The reaction mixture was stirred and irradiated by a 50 W light source with a wavelength of 395 nm to 405 nm for 8 h. The reaction was terminated, and the reaction mixture was extracted with dichloromethane (10 mL×3). The liquid chromatography normalization method analysis showed that p-fluorobenzoic acid had a relative content of 59.2%. A dichloromethane layer was thoroughly washed with a saturated sodium carbonate water solution (5 mL×2). The resulted water layers were combined and acidified to pH=2 to 3 with 10% sulfuric acid. The mixture was filtered, and the obtained filter cake was dried to obtain 0.7 g of a white p-fluorobenzoic acid solid with an isolated yield of 50%, having a purity of 94.0% by the liquid chromatography external standard analysis.

Example 7

Acid-Catalyzed Photo-Oxidation of 2,4-dichlorotoluene 1 mmol of trifluoromethanesulfonic acid, 5 mL of water, and 10 mmol of 2,4-dichlorotoluene were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W light source with a wavelength of 350 nm to 370 nm for 18 h. The reaction was monitored by LC-MS with deduction of the solvent absorption, consisting of 71.8% of 2,4-dichlorobenzoic acid, 0.7% of 2,4-dichlorobenzyl alcohol, 0.9% of 2,4-dichlorobenzaldehyde, and 8.7% of 2,2',4,4'-tetrachlorobibenzyl. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 1.18 g of a white 2,4-dichlorobenzoic acid solid with an isolated yield of 62%, having a purity of 96.4% by the liquid chromatography external standard analysis.

Example 8

Acid-Catalyzed Photo-Oxidation of 2-chloro-4-fluorotoluene 2 mmol of N-butylsulfonate pyridinium hydrogensulfate, 2 mL of water, 10 mmol of 2-chloro-4-fluorotoluene, and 7 mL of acetonitrile were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W light source with a wavelength of 350 nm to 370 nm for 12 h. The reaction was monitored by LC-MS with deduction of the solvent absorption, consisting of 55.1% of 2-chloro-4-fluorobenzoic acid, 0.5% of 2-chloro-4-fluorobenzyl alcohol, and 0.5% of 2-chloro-4-fluorobenzaldehyde. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 0.85 g of a white 2-chloro-4-fluorobenzoic acid solid with an isolated yield of 49%, having a purity of 96.8% by the liquid chromatography external standard analysis.

Example 9

Acid-Catalyzed Photo-Oxidation of 2,3,5-trichlorotoluene 1.5 mmol of N-propylsulfonate pyridinium hydrogensulfate, 5 mL of water, 10 mmol of 2,3,5-trichlorotoluene, and 5 mL of 2-butanone were sequentially added to a 25 mL colorless and transparent ground quartz tube with a built-in magnetic stirring bar. The test tube was connected to an oxygen-filled balloon by a tee. The reaction mixture was stirred and irradiated by a 50 W light source with a wavelength of 350 nm to 370 nm for 24 h. The reaction was monitored by LC-MS with deduction of the liquid phase normalization method, consisting of 77.5% of 2,3,5-trichlorobenzoic acid. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 1.56 g of a white 2,3,5-trichlorobenzoic acid solid with an isolated yield of 69.2%, having a purity of 94.8% by the liquid chromatography external standard analysis.

Example 10

Acid-Catalyzed Photo-Oxidation of p-methylanisole 1 mmol of N-propylsulfonate pyridinium tetrafluoroborate, 2 mL of water, 10 mmol of p-methylanisole, and 3 mL of acetonitrile were sequentially added to a 25 mL colorless and transparent ground quartz tube with a built-in magnetic stirring bar. The test tube was mounted with a reflux condenser. The reaction mixture was stirred and irradiated by a 50 W light source with a wavelength of 350 nm to 370 nm for 32 h. The reaction was monitored by LC analysis with deduction of the solvent absorption, consisting of 86.5% of 4-methoxybenzoic acid. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 1.18 g of a white 4-methoxybenzoic acid solid with an isolated yield of 78.2%, having a purity of 97.3% by the liquid chromatography external standard analysis.

Example 11

Acid-Catalyzed Photo-Oxidation of m-trifluoromethyltoluene 1 mmol of N-butylsulfonate pyridinium trifluoromethanesulfonate, 5 mL of water, 10 mmol of m-trifluoromethyltoluene, and 3 mL of acetonitrile were sequentially added to a 25 mL colorless and transparent ground quartz tube with a built-in magnetic stirring bar. The test tube was mounted with a reflux condenser. The reaction mixture was stirred and irradiated by a 50 W light source with a wavelength of 350 nm to 370 nm for 22 h. The method was monitored by liquid chromatography with deduction of the solvent absorption, consisting of 85.3% of m-trifluoromethylbenzoic acid. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 1.44 g of a white m-trifluoromethylbenzoic acid solid with an isolated yield of 75.9%, having a purity of 98.0% by the liquid chromatography external standard analysis.

Example 12

Acid-Catalyzed Photo-Oxidation of 3,4-dichlorotoluene 2 mmol of p-toluenesulfonic acid, 10 mmol of 3,4 dichlorotoluene, and 5 mL of chlorobenzene were sequentially added to a 25 mL colorless and transparent ground quartz tube with a built-in magnetic stirring bar. The test tube was mounted with a reflux condenser. The reaction mixture was stirred and irradiated by a 50 W light source with a wavelength of 350 nm to 370 nm for 24 h. The reaction was monitored by LC-MS with deduction of the solvent absorption, consisting of 3,4-dichlorobenzoic acid with a normalized content of 24.8%.

Example 13

Catalytic Photo-Oxidation of 4-trifluoromethyltoluene 2 mmol of trifluoromethanesulfonic acid, 10 mmol of 4-trifluoromethyltoluene, 5 mL of dichloroethane were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W light source with a wavelength of 350 nm to 370 nm for 24 h. The reaction was monitored by LC-MS with deduction of the solvent absorption, consisting of 4-trifluoromethylbenzoic acid with a normalized content of 33.6%.

Example 14

Catalytic Photo-Oxidation of 4-trifluoromethyltoluene 1 mmol of trifluoromethanesulfonic acid, 10 mmol of 4-trifluoromethyltoluene, 5 mL of acetonitrile were sequentially added to a 25 mL colorless and transparent ground quartz tube with a built-in magnetic stirring bar. The test tube was connected to a tee and then connected with an oxygen-filled balloon. The reaction mixture was stirred and irradiated by a 50 W light source with a wavelength of 350 nm to 370 nm for 14 h. The reaction was monitored by LC-MS with deduction of the solvent absorption, consisting of 4-trifluoromethylbenzoic acid with a normalized content of 55.5%.

Example 15

Acid-Catalyzed Photo-Oxidation of 4-bromoethylbenzene 1 mmol of sulfuric acid, 3 mL of water, 10 mmol of 4-bromoethylbenzene, and 7 mL of acetonitrile were sequentially added to a 25 mL colorless and transparent ground quartz tube with a built-in magnetic stirring bar. A condenser was attached to the test tube for air communication. The reaction mixture was stirred and irradiated by a 50 W UV light source with a wavelength of 350 nm to 370 nm for 12 h. The reaction was monitored by GC-MS with deduction of the solvent absorption, consisting of 70.7% of 4-bromoacetophenone.

Example 16

Acid-Catalyzed Photo-Oxidation of Ethylbenzene 1 mmol of hydrochloric acid, 3 mL of water, 10 mmol of ethylbenzene, and 5 mL of acetonitrile were sequentially added to a 25 mL colorless and transparent ground quartz tube with a built-in magnetic stirring bar. A condenser was attached to the test tube for air communication. The reaction mixture was stirred and irradiated by a 50 W UV light source with a wavelength of 350 nm to 370 nm for 16 h. The reaction was monitored by GC-MS with deduction of the solvent absorption, consisting of 81.5% of acetophenone.

Example 17

Acid-Catalyzed Photo-Oxidation Of p-chloroethylbenzene 1 mmol of N-butylsulfonate pyridinium tetrafluoroborate, 1 mL of water, 10 mmol of p-chloroethylbenzene, 6 mL of acetonitrile were sequentially added to a 25 mL colorless and transparent ground quartz tube with a built-in magnetic stirring bar. A condenser was attached to the test tube for air communication. The reaction mixture was stirred and irradiated by a 50 W UV light source with a wavelength of 395 nm to 405 nm for 8 h. The reaction was monitored by GC-MS with deduction of the solvent absorption, consisting of 64.5% of p-chloroacetophenone.

Example 1

Acid-Catalyzed Photo-Oxidation of p-nitroethylbenzene 1 mmol of N-butylsulfonate pyridinium tetrafluoroborate, 1 mL of water, 10 mmol of p-nitroethylbenzene, and 6 mL of acetonitrile were sequentially added to a 25 mL colorless and transparent ground quartz tube with a built-in magnetic stirring bar. The top of the test tube was mounted with a condenser. The reaction mixture was stirred and irradiated by a 50 W UV light source with a wavelength of 350 nm to 370 nm for 8 h. The reaction was monitored by GC-MS with deduction of the solvent absorption, consisting of 20.4% of p-nitroacetophenone.

Example 19

Acid-Catalyzed Photo-Oxidation of p-nitroethylbenzene 1 mmol of triflic acid, 1 mL of water, 10 mmol of p-nitroethylbenzene, and 6 mL of acetonitrile were sequentially added to a 25 mL colorless and transparent ground quartz tube with a built-in magnetic stirring bar. The top of the test tube was mounted with a condenser, the air was slowly introduced from above with a silicone tube. The reaction mixture was stirred and irradiated by a 50 W UV light source with a wavelength of 350 nm to 370 nm for 12 h. The reaction was monitored by GC-MS with deduction of the solvent absorption, consisting of 33.6% of p-nitroacetophenone.

Example 20

Acid-Catalyzed Photo-Oxidation of m-nitroethylbenzene 2 mmol of trifluoroacetic acid, 10 mmol of m-nitroethylbenzene, and 5 mL of acetonitrile were sequentially added to a 25 mL colorless and transparent ground quartz tube with a built-in magnetic stirring bar. The test tube was mounted with a reflex condenser, and then connected with an oxygen-filled balloon by a tee. The reaction mixture was stirred and irradiated by a 50 W light source with a wavelength of 350 nm to 370 nm for 12 h. The reaction was monitored by LC-MS with deduction of the solvent absorption, consisting of m-nitroacetophenone with a normalized content of 45.1%.

Example 21

Acid-Catalyzed Photo-Oxidation of p-diethylbenzene 2 mmol of methanesulfonic acid, 10 mmol of p-diethylbenzene, and 5 mL of acetonitrile were sequentially added to a 25 mL colorless and transparent ground quartz tube with a built-in magnetic stirring bar. The test tube was mounted with a reflex condenser, and then connected with an oxygen-filled balloon by a tee. The reaction mixture was stirred and irradiated by a 50 W light source with a wavelength of 350 nm to 370 nm for 12 h. The reaction was monitored by GC-MS with deduction of the solvent absorption, consisting of 67.0% of p-ethylacetophenone and 12.0% of p-diacetylbenzene.

Example 22

Acid-Catalyzed Photo-Oxidation of Cumene 2 mmol of sulfuric acid, 3 mL of water, 10 mmol of cumene, and 5 mL of acetonitrile were sequentially added to a 25 mL colorless and transparent ground quartz tube with a built-in magnetic stirring bar. Test tube was mounted with a reflex condenser, and then connected with an oxygen-filled balloon by a tee. The reaction mixture was stirred and irradiated by a 50 W light source with a wavelength of 350 nm to 370 nm for 12 h. The reaction was monitored by GC-MS with deduction of the solvent absorption, consisting of acetophenone with a normalized content of 69.1%.

Example 23

Acid-Catalyzed Photo-Oxidation of Cumene 1 mmol of trifluoromethanesulfonic acid, 10 mmol of cumene, and 5 mL of acetonitrile were sequentially added to a 25 mL colorless and transparent ground quartz tube with a built-in magnetic stirring bar. the test tube was mounted with a reflex condenser, and then connected with an oxygen-filled balloon by a tee. The reaction mixture was stirred and irradiated by a 50 W light source with a wavelength of 350 nm to 370 nm for 12 h. The reaction was monitored by LC-MS with deduction of the solvent absorption, consisting of acetophenone with a normalized content of 64.8%.

Example 24

Acid-Catalyzed Photo-Oxidation of 4-bromocumene 1 mmol of trifluoromethanesulfonic acid, 10 mmol of 4-bromocumene, and 5 mL of acetonitrile were sequentially added to a 25 mL colorless and transparent ground quartz tube with a built-in magnetic stirring bar. A reflux condenser was mounted at the test tube, and air was slowly blown in from a bottom of the reaction solution with an air tube. The reaction mixture was stirred and irradiated by a 50 W light source with a wavelength of 395 nm to 405 nm for 16 h. The reaction was monitored by LC-MS with deduction of the solvent absorption, consisting of 4-bromoacetophenone with a normalized content of 73.5%.

Example 25

Acid-Catalyzed Photo-Oxidation of p-toluic Acid 0.1 mmol of trifluoromethanesulfonic acid, 1.0 mmol of p-toluic acid, and 5 mL of acetone were sequentially added to a 25 mL colorless and transparent ground quartz test tube with a built-in magnetic stirring bar. The test tube was connected to a tee and then connected with an oxygen-filled balloon. The reaction mixture was stirred and irradiated by a 50 W light source with a wavelength of 350 nm to 370 nm for 24 h. The reaction was terminated, the solvent was removed by rotary evaporation under reduced pressure, and a resulted residue was purified by column chromatography (Silica gel column chromatography silicon, eluent: petroleum ether/ethyl acetate/HOAc=20/20/1 (v/v/v)) to obtain 92 mg of p-phthalic acid with an isolated yield of 56%, having a purity of 96.9% by the liquid chromatography external standard analysis.

Example 26

Acid-Catalyzed Photo-Oxidation of 4-methyl Diphenyl 0.1 mmol of tetrafluoroboric acid, 1.0 mmol of 4-methyl diphenyl, and 5 mL of acetone were sequentially added to a 25 mL colorless and transparent ground quartz test tube with a built-in magnetic stirring bar. The test tube was connected to a tee and then connected with an oxygen-filled balloon. The reaction mixture was stirred and irradiated by a 50 W light source with a wavelength of 350 nm to 370 nm for 16 h. The reaction was terminated, the solvent was removed by rotary evaporation under reduced pressure, and a resulted residue was purified by column chromatography (Silica gel column chromatography silicon, eluent: petroleum ether/ethyl acetate/HOAc=30/10/1 (v/v/v)) to obtain 147 mg of biphenyl-4-carboxylic acid with an isolated yield of 75%, having a purity of 98.5% by the liquid chromatography external standard analysis.

Example 27

Acid-Catalyzed Photo-Oxidation of 4-methylbenzonitrile 1 mmol of trifluoromethanesulfonic acid, 10 mmol of 4-trifluoromethyltoluene, and 10 mL of acetonitrile were sequentially added to a 25 mL colorless and transparent ground quartz test tube with a built-in magnetic stirring bar. The test tube was connected to a tee and then connected with an oxygen-filled balloon. The reaction mixture was stirred and irradiated by a 50 W light source with a wavelength of 350 nm to 370 nm for 14 h. The reaction was terminated, and the acetonitrile was removed by rotary evaporation under reduced pressure; and the reaction mixture was extracted with ethyl acetate (10 mL×3). The organic layers were combined, and then washed thoroughly with a saturated sodium carbonate water solution (5 mL×2). The resulted water layers were combined and acidified to pH=2 to 3 with 10% hydrochloric acid. The mixture was filtered, and the obtained filter cake was dried to obtain 0.82 g of 4-cyanobenzoic acid with an isolated yield of 55.5%, having a purity of 97.8% by the liquid chromatography external standard analysis.

The foregoing are merely descriptions of preferred specific implementations of the present disclosure, but the protection scope of the present disclosure is not limited thereto. Any equivalent replacement or modification made within a technical scope of the present disclosure by a person skilled in the art according to the technical solutions of the present disclosure and inventive concepts thereof shall fall within the protection scope of the present disclosure.

INDUSTRIAL APPLICABILITY

In the present disclosure, the acid-catalyzed photo-oxidation reaction of methylarenes has significant technical advantages, and its oxidation process has no metal participation, no chemical oxidant, mild reaction conditions, fast conversion, and high selectivity. In addition, the catalyst is not consumed and can be easily recovered. Meanwhile, photocatalytic molecular oxidation and electrochemical oxidation processes have high atom economy, clean process, and low-cost oxidant, showing a desirable prospect of industrial application, such that these processes have significant advantages in safety, environmental protection, economic and social benefits.

What is claimed is:
1. An acid-catalyzed photocatalyzed oxidation reaction of benzylic C—H bonds of an aromatic compound, wherein the liquid-phase oxidation reaction is conducted with oxygen or air as the oxidants using Bronsted acid as the photocatalyst at normal pressure under light irradiation with a wavelength range of 300 nm to 450 nm.

2. The acid-catalyzed photocatalyzed oxidation reaction of benzylic C—H bonds of an aromatic compound according to claim 1, wherein the Bronsted acid is one or a mixture of two or more selected from the group consisting of an inorganic acid, an organic acid, and an acidic ionic liquid.

3. The acid-catalyzed photocatalyzed oxidation reaction of benzylic C—H bonds of an aromatic compound according to claim 1, wherein the Bronsted acid is one or a mixture of two or more selected from the group consisting of hydrochloric acid, phosphoric acid, sulfuric acid, p-toluenesulfonic acid, methanesulfonic acid, trifluoromethanesulfonic acid, trifluoroacetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

4. The acid-catalyzed photocatalyzed oxidation reaction of benzylic C—H bonds of an aromatic compound according to claim 1, wherein the Bronsted acid is one or a mixture of two or more selected from the group consisting of hydrochloric acid, sulfuric acid, tetrafluoroboric acid, p-toluenesulfonic acid, methanesulfonic acid, trifluoromethanesulfonic acid, trifluoroacetic acid, acetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

5. The acid-catalyzed photocatalyzed oxidation reaction of benzylic C—H bonds of an aromatic compound according to claim 1, wherein the aromatic compound is one selected from the group consisting of methylarenes, ethylarenes, and cumenes that contains at least one benzylic C—H bond.

6. The acid-catalyzed photocatalyzed oxidation reaction of benzylic C—H bonds of an aromatic compound according to claim 1, wherein the aromatic compound is selected from the group consisting of the methylarenes, the ethylarenes, and the cumenes; the methylarenes are selected from the group consisting of toluene, o-xylene, m-xylene, p-xylene, mesitylene, toluene substituted with 1 to 3 halogen atoms, toluene substituted with alkoxy of 1 to 2 C atoms, and trifluoromethyl-substituted toluene; the ethylarenes are selected from the group consisting of ethylbenzene, p-diethylbenzene, ethylbenzene substituted with 1 to 3 halogen atoms, ethylbenzene substituted with alkoxy of 1 to 2 C atoms, trifluoromethyl-substituted ethylbenzene, and nitro-substituted ethylbenzene; and the cumenes are selected from the group consisting of cumene, halogen-substituted cumene, trifluoromethyl-substituted cumene, and nitro-substituted cumene.

7. The acid-catalyzed photocatalyzed oxidation reaction of benzylic C—H bonds of an aromatic compound according to claim 1, wherein the aromatic compound is selected from the group consisting of the methylarenes, the ethylarenes, and the cumenes; the methylarenes are any one selected from the group consisting of toluene, o-xylene, m-xylene, p-xylene, mesitylene, toluene substituted with 1 to 3 halogen atoms, toluene substituted with alkoxy of 1 to 2 C atoms, trifluoromethyl-substituted toluene, o-tolunitrile, m-tolunitrile, p-tolunitrile, o-toluic acid, m-toluic acid, p-toluic acid, 2-methyl diphenyl, 3-methyl diphenyl, and 4-methyl diphenyl; the ethylarenes are any one selected from the group consisting of ethylbenzene, p-diethylbenzene, ethylbenzene substituted with 1 to 3 halogen atoms, ethylbenzene substituted with alkoxy of 1 to 2 C atoms, trifluoromethyl-substituted ethylbenzene, and nitro-substituted ethylbenzene; and the cumenes are any one selected from the group consisting of cumene, halogen-substituted cumene, trifluoromethyl-substituted cumene, and nitro-substituted cumene.

8. The acid-catalyzed photocatalyzed oxidation reaction of benzylic C—H bonds of an aromatic compound according to claim 1, wherein the oxidation reaction is conducted in a solvent; the solvent is selected from the group consisting of water, dichloromethane, dichloroethane, benzene, chlorobenzene, acetonitrile, acetone, 2-butanone, and the ionic liquid; and the ionic liquid is one selected from the group consisting of N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate, or is a mixture of two of the above-described solvents.

9. The acid-catalyzed photocatalyzed oxidation reaction of benzylic C—H bonds of an aromatic compound according to claim 1, wherein the oxidation reaction is conducted in a solvent, and the solvent is selected from the group consisting of water, the organic solvent, and the ionic liquid, or is a mixture of any two of the above-described solvents.

10. The acid-catalyzed photocatalyzed oxidation reaction of benzylic C—H bonds of an aromatic compound according to claim 1, wherein the oxidation reaction is conducted in the solvent; the Bronsted acid comprises the inorganic acid; the solvent is selected from the group consisting of water, the organic solvent, or a mixture of water and the organic solvent.

11. The acid-catalyzed photocatalyzed oxidation reaction of benzylic C—H bonds of an aromatic compound according to claim 1, wherein the oxidation reaction is conducted in the solvent; the Bronsted acid comprises the organic acid; the solvent is selected from the group consisting of the organic solvent and the mixture of the organic solvent and water.

12. The acid-catalyzed photocatalyzed oxidation reaction of benzylic C—H bonds of an aromatic compound according to claim 1, wherein the oxidation reaction is conducted in the solvent; the Bronsted acid comprises a strongly-acidic ionic liquid; and the solvent is a mixture of one selected from the group consisting of the dichloromethane, the dichloroethane, the benzene, the chlorobenzene, and the chloroform with water.

13. The acid-catalyzed photocatalyzed oxidation reaction of benzylic C—H bonds of an aromatic compound according to claim 1, wherein the Bronsted acid is used with an amount of 0.1% mol to 20% mol of the aromatic compound.

14. The acid-catalyzed photocatalyzed oxidation reaction of benzylic C—H bonds of an aromatic compound according to claim 1, wherein the Bronsted acid is used with an amount of 0.5% mol to 5% mol of the aromatic compound.

15. The acid-catalyzed photocatalyzed oxidation reaction of benzylic C—H bonds of an aromatic compound according to claim 7, wherein a product obtained by photo-oxidation of the methylarenes under acid catalysis is a corresponding substituted or unsubstituted aryl fomic acid; a product obtained by photo-oxidation of the ethylarenes under acid catalysis is a corresponding substituted or unsubstituted acetophenone; and a product obtained by photo-oxidation of the cumenes under acid catalysis is a corresponding acetophenone.

16. The acid-catalyzed photocatalyzed oxidation reaction of benzylic C—H bonds of an aromatic compound according to claim 1, wherein the oxidation reaction is conducted at 10° C. to 100° C.

17. The acid-catalyzed photocatalyzed oxidation reaction of benzylic C—H bonds of an aromatic compound according to claim 1, wherein the oxidation reaction is conducted at 20° C. to 60° C.

18. The acid-catalyzed photocatalyzed oxidation reaction of benzylic C—H bonds of an aromatic compound according to claim 2, wherein the Bronsted acid is one or a mixture of two or more selected from the group consisting of hydrochloric acid, phosphoric acid, sulfuric acid, p-toluenesulfonic acid, methanesulfonic acid, trifluoromethanesulfonic acid, trifluoroacetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

19. The acid-catalyzed photocatalyzed oxidation reaction of benzylic C—H bonds of an aromatic compound according to claim 2, wherein the Bronsted acid is one or a mixture of two or more selected from the group consisting of hydrochloric acid, sulfuric acid, tetrafluoroboric acid, p-toluenesulfonic acid, methanesulfonic acid, trifluoromethanesulfonic acid, trifluoroacetic acid, acetic acid, and potassium hydrogen sulfate, as well as N-propylsulfonate pyridinium hydrogensulfate, N-butylsulfonate pyridinium hydrogensulfate, N-propylsulfonate pyridinium trifluoromethanesulfonate, N-butylsulfonate pyridinium trifluoromethanesulfonate, N-propylsulfonate pyridinium tetrafluoroborate, and N-butylsulfonate pyridinium tetrafluoroborate.

20. The acid-catalyzed photocatalyzed oxidation reaction of benzylic C—H bonds of an aromatic compound according to claim 2, wherein an aromatic compound is one selected from the group consisting of methylarenes, ethylarenes, and cumenes that contains one benzylic C—H bond.

* * * * *